United States Patent
Jeon et al.

(10) Patent No.: US 8,759,461 B2
(45) Date of Patent: *Jun. 24, 2014

(54) POST METALLOCENE-TYPE TRANSITION METAL COMPOUNDS

(75) Inventors: Sang-Jin Jeon, Daejeon (KR); Hoon Chae, Daejeon (KR); Cheon-Il Park, Daejeon (KR); Kyung-Seop Noh, Daejeon (KR); Won-Hee Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 195 days.

This patent is subject to a terminal disclaimer.

(21) Appl. No.: 13/386,282

(22) PCT Filed: Jul. 23, 2010

(86) PCT No.: PCT/KR2010/004842
§ 371 (c)(1),
(2), (4) Date: Jan. 20, 2012

(87) PCT Pub. No.: WO2011/010891
PCT Pub. Date: Jan. 27, 2011

(65) Prior Publication Data
US 2012/0196994 A1    Aug. 2, 2012

(30) Foreign Application Priority Data
Jul. 23, 2009  (KR) .................. 10-2009-0067395

(51) Int. Cl.
C08F 4/76   (2006.01)
C08F 4/64   (2006.01)
C08F 4/52   (2006.01)

(52) U.S. Cl.
USPC ........... 526/172; 526/161; 526/170; 526/160; 526/134; 526/348; 556/51

(58) Field of Classification Search
USPC .................... 556/51; 526/172, 161
See application file for complete search history.

(56) References Cited

FOREIGN PATENT DOCUMENTS

| JP | 2002-256013 A | * | 9/2002 | ............. C08F 4/625 |
| JP | 2002-363210 | | 12/2002 | |
| JP | 2004-323806 A | * | 11/2004 | ............. C08F 4/625 |
| WO | 2008/140205 | | 11/2008 | |

OTHER PUBLICATIONS

JP 2002-256013 (Matsuki et al., Sep. 11, 2002) abstract and translation in English.*
JP 2004-323806 (Ono et al., Nov. 18, 2004) abstract and translation in English.*
Kochnev et al. Russian J. Organic Chem., 2007, 43, 571-575.*
Yang et al. J. Polym. Sci. Part A: Polym. Chem. 2008, 46, 5251-5262.*
Ho et al. Organometallics, 2006, 25, 5800-5810.*
"Design of Schiff Base-Like Postmettalocene Catalytic Systems for Polymerization of Olefins: II. Synthesis of 2, 6-Bis(aryliminoalkyl) pyridines with Cycloalkyl Substituents"; Russian Journal of General Chemistry. Vo. 74. No. 10, 2004. pp. 1575-1578.
Heimo Woefle; On the Way to Biodegradable Poly(Hydroxy Butyrate) . . . , Journal of Organometallic Chemistry, Jul. 15, 2009, vol. 694, No. 16, pp. 2493-2512, ISSN 0022-328X.
Kochnev, A. I., et al.; Design of Schiff Base-Like Postmetallocene Catalytic Systems for Polymerization of Olefins: IV. Synthesis of 2-arylimionomethyl)pyrrole and 7-(aryliminomethyl)indole derivatives . . . ; Russian Journal of Organic Chemistry, 2007, vol. 43, No. 4, pp. 571-575, ISSN 1070-4280.

* cited by examiner

*Primary Examiner* — Rip A. Lee
(74) *Attorney, Agent, or Firm* — McKenna Long & Aldridge, LLP

(57) ABSTRACT

The present invention relates to a novel post metallocene-type ligand compound, to a metal compound containing the ligand compound, to a catalytic composition containing the metal compound, and to a method for preparing same, as well as to a method for preparing olefin polymers using the catalytic composition. The present invention provides a catalyst for preparing special polyolefin-based polymers having excellent activity.

19 Claims, No Drawings

POST METALLOCENE-TYPE TRANSITION METAL COMPOUNDS

This application is a National Stage Entry of International Application No. PCT/KR2010/004842, filed Jul. 23, 2010, and claims the benefit of Korean Application No. 10-2009-0067395, filed on Jul. 23, 2009, which is hereby incorporated by reference for all purposes as if fully set forth herein.

TECHNICAL FIELD

The present invention relates to a novel post metallocene ligand compound, an organometallic compound comprising the novel ligand compound, a catalyst composition comprising the organometallic compound and a production method thereof, and a process for preparing olefin polymers by using the catalyst composition.

BACKGROUND OF THE ART

A constrained-geometry catalyst (CGC) [Me$_2$Si($\eta^5$-Me$_4$C$_5$)NtBu]TiCl$_2$ is one of the most typical and most representative, commercialized catalysts among homogeneous Ziegler-Natta olefinic polymerization catalyst (metallocene catalyst) systems. A cocatalyst-activated CGC has the following advantages over the conventional metallocene catalysts: (1) it shows a high level of activity even at a higher polymerization temperature, allowing the production of high molecular weight polymers, and (2) it also provides an excellent degree of copolymerization for sterically hindered α-olefinic monomers such as 1-hexene and 1-octene. Besides, as various characteristics thereof became known in the art, vigorous efforts was made in the academic and industrial circles to synthesize and use CGC catalyst derivatives as a polymerization catalyst for different purposes (*Chem. Rev.*, 2003, 103, 283).

Meanwhile, a Group IV transition metal compound (Tr, Zr) including a phenoxy imine moiety as its basic skeleton was developed by Mitzui Co. Ltd. (Japan), showing an excellent activity and capability such as various control, living polymerizations of polypropylene as well as polyethylene. The catalyst is characterized in that its structure is free from a cyclopentadienyl ligand, the major skeleton of the conventional metallocene catalyst or the CGC. For that reason, this catalyst came into the spotlight as a post metallocene catalyst, i.e., a next generation catalyst departing from the metallocene structure. Thereafter, it was denominated as "FI catalyst," and its activity and effectiveness depending on various substituents surrounding the basic skeleton of the catalyst was carefully scrutinized. Up to date, it has been cited in numerous references. (*J. Am. Chem. Soc.* 2001, 123, 6847 and 2002, 124, 3327).

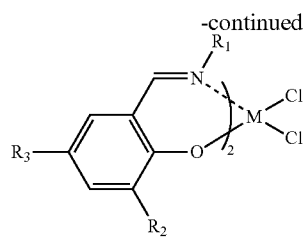

M = Ti, Zr, Hf
FI catalyst

Recently, LG Chem. Ltd. developed some catalysts with a ligand wherein a phenyl group was introduced into a CGC backbone as another bridge (*Organometallics*, 2006, 25, 5122 and 2008, 27, 3907). In current levels of preparing an ethylene/1-octene copolymer, this catalyst exhibited an activity, a molecular weight, and the content of 1-octene that are equal to or higher than that of the conventional CGC.

[FIG. 2]

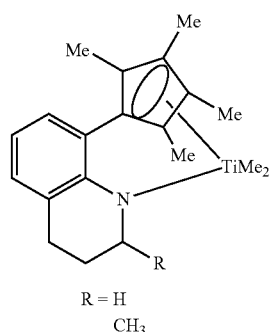

R = H
CH$_3$
(CH$_2$)$_2$CH$_3$
(CH$_2$)$_6$O$^t$Bu

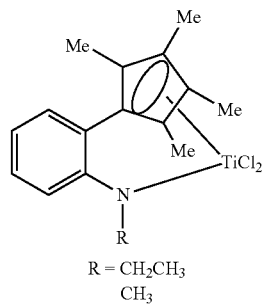

R = CH$_2$CH$_3$
CH$_3$

[FIG. 1]

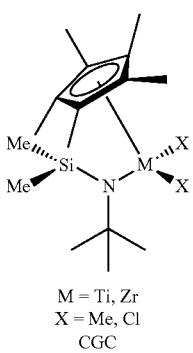

M = Ti, Zr
X = Me, Cl
CGC

SUMMARY OF THE INVENTION

The present invention provides a next generation, post metallocene catalyst by introducing a ligand with a novel structure other than a cyclopentadienyl ring that has served as a basis for the conventional CGC in the conventional catalyst structure for preparing a copolymer as shown in FIG. 2.

Accordingly, the present invention provides a novel ligand prepared by using a hydroquinoline as a starting material and introducing an aldehyde group into one side of a phenyl ring, and a multi-chelate ligand compound for various post-metallocene catalyst derived therefrom.

Further, the present invention provides a metallic compound having a Group IV metal as a central metal prepared by using the aforementioned ligand.

Further, the present invention provides a catalyst composition comprising the aforementioned metallic compound, a production method thereof, and a process for preparing olefin polymers by using the same.

An aspect of the present invention provides a compound as represented by Chemical Formula 1:

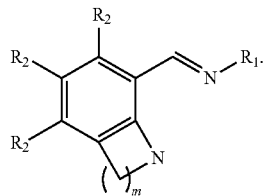

[Chemical Formula 1]

In Chemical Formula 1, m is an integer of 1 to 7;

$R_1$ is a C4-C10 cycloalkyl group substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group; a C2-C9 heterocyclic group with a heteroatom of O, N or S, substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group; a C6-C10 aryl group substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group; or a C5-C10 heteroaryl group with a heteroatom of O, N or S, substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group, and when the $R_1$ is substituted with at least two groups, the groups that are adjacent to each other can form an aliphatic or aromatic condensed ring;

$R_2$s are the same with or different from each other, and are independently selected from the group consisting of hydrogen, deuterium, a halogen group, a nitrile group, an acetylene group, an amine group, an amide group, an ester group, a ketone group, a C1-C20 alkyl group, a C2-C20 alkenyl group, a C6-C20 aryl group, a C4-C20 heterocyclic group, a C1-C20 alkoxy group and a C6-C20 aryloxy group, respectively, and at least two of the $R_2$s can be linked to each other to form an aliphatic or aromatic ring.

A second aspect of the present invention provides a metallic compound coordinated by a transition metal of Group IV comprising the foregoing compound as a ligand.

A third aspect of the present invention provides a catalyst composition comprising the aforementioned metallic compound, a compound represented by Chemical Formula 4, and a compound represented by Chemical Formula 5:

[Chemical Formula 4]

In the above formula, $R_3$s are independently a halogen radical or a C1-C20 hydrocarbyl radical substituted with a halogen, respectively.

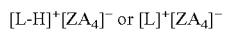

[Chemical Formula 5]

In the above formula, L is a neutral or cationic Lewis acid; and H is a hydrogen atom; Z is an element of Group 13; and As are independently a C6-C20 aryl or an alkyl radical substituted with a halogen, a C1-C20 hydrocarbyl, an alkoxy, or a phenoxy radical for at least one hydrogen atom therein.

A fourth aspect of the present invention provides a production method of the aforementioned catalyst composition.

A fifth aspect of the present invention provides a process for preparing olefin polymers by using the aforementioned catalyst composition.

ADVANTAGEOUS EFFECT OF THE INVENTION

According to the present invention, it is possible to provide a highly active catalyst for preparing special polyolefinic polymers.

BEST MODES FOR PRACTICING THE INVENTION

Hereinafter, the present invention will be explained in further detail.

An aspect of the present invention is directed to a compound as represented by Chemical Formula 1.

Regarding the above chemical formula, detailed explanations for each substituent are as follows.

The C1-C20 alkyl group includes an alkyl group in the form of a straight chain or a branched chain.

The C1-C20 alkenyl group includes an alkenyl group in the form of a straight chain or a branched chain.

Examples of the silyl group include, but are not limited to, trimethylsilyl, triethylsilyl, tripropylsilyl, tributylsilyl, trihexylsilyl, triisopropylsilyl, triisobutylsilyl, triethoxysilyl, triphenylsilyl, and tris(trimethylsilyl)silyl.

Preferably, the aryl group has 6 to 20 carbon atoms, and its examples include, but are not limited to, phenyl, naphthyl, anthracenyl, pyridyl, dimethylanilinyl, anisolyl, and the like.

The alkylaryl group refers to an aryl group substituted with an alkyl group.

The arylalkyl group refers to an alkyl group substituted with the aryl group.

The halogen group refers to a fluorine group, a chlorine group, a bromine group, or an iodine group.

The alkyl amino group refers to an amino group substituted with the alkyl group, and its examples include, but are not limited to, dimethylamino group, diethylamino group, and the like.

The aryl amino group refers to an amino group substituted with the aryl group, and its examples include, but are not limited to, diphenylamino group and the like.

The compound represented by Chemical Formula 1 can be a compound represented by Chemical Formula 2 or Chemical Formula 3 as follows:

[Chemical Formula 2]

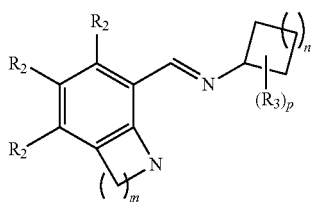

[Chemical Formula 3]

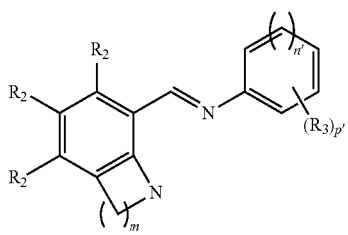

In Chemical Formula 2 or Chemical Formula 3,
m and $R_2$ are the same as defined in Chemical Formula 1,
n is an integer of 1 to 7,
n' is an integer of 1 to 5,
p is an integer of 0 to 2+n,
p' is an integer of 0 to 5+n',
$R_3$s are the same with or different from each other, and are independently selected from the group consisting of deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group, and at least two of the R3s can be linked to each other to form an aliphatic or aromatic condensed ring. In particular, it is preferable that the $R_3$s are a C1-C20 alkyl group, a C6-C20 cycloalkyl group, a C2-C20 alkenyl group, or a C6-C20 aryl group, and at least two of the $R_3$s can be linked to each other to form an aliphatic or aromatic condensed ring.

In Chemical Formulas 1 to 3, m is preferably 2 or 3. In addition, in Chemical Formula 2 or Chemical Formula 3, n is preferably 2 or 3. In addition, in Chemical Formula 2 or Chemical Formula 3, n' is preferably an integer of 1 to 3.

Specific examples of the compound represented by Chemical Formula 1 include, but are not limited to, any compound represented by any one of the following structural formulas:

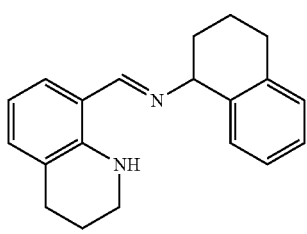

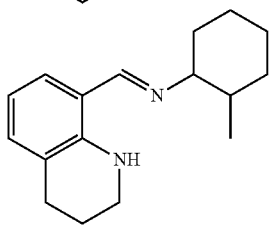

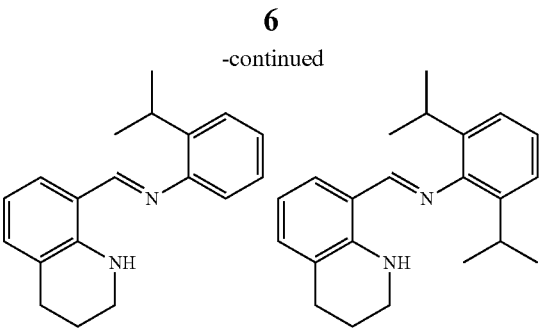

A typical production method of the compound represented by Chemical Formula 1 is as follows, but the present invention is not limited thereto:

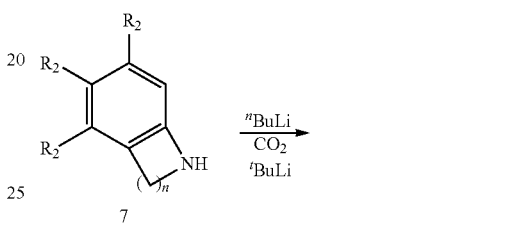

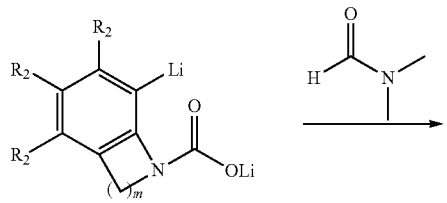

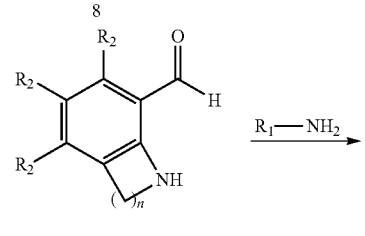

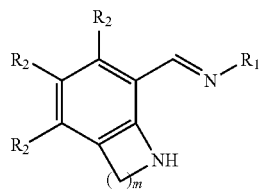

chemical Formula I

In the above production method, $R_1$ and $R_2$ are the same as defined in Chemical Formula 1.

In the above production method, with Compound 7 being employed as a starting material, Intermediate Compound 8 can be synthesized by adopting a selective lithium substitution method, and then reacted with DMF (N,N-Dimethylformamide) to prepare Compound 9. Thereafter, Compound 9 can be reacted with $R_1$—$NH_2$ under a reflux or with stirring to obtain the compound represented by Chemical Formula 1. In particular, with regard to $R_1$—$NH_2$, when $R_1$ is an aryl group, one can obtain the resulting product by introducing 4A MS and then refluxing the mixture overnight, and when $R_1$ is an alkyl group or an alkylaryl group, one can obtain the resulting product by stirring the mixture overnight at room temperature.

Depending on the types of $R_1$, the compound represented by Chemical Formula 1 prepared according to the above methods can be a ligand compound capable of forming a two-site chelate (NN chelate) with a metal or a ligand compound capable of forming an at least three site chelate (NNN, NNO, or NNC).

A second aspect of the present invention is directed to an organometallic compound coordinated by a transition metal of Group IV comprising the above compound as a ligand.

Examples of the transition metal includes, but are not limited to, Ti, Zr, Hf, and the like.

The metallic compound can be represented by any one of the following structural formulas, but the present invention is not limited thereto:

[FIG. 4]

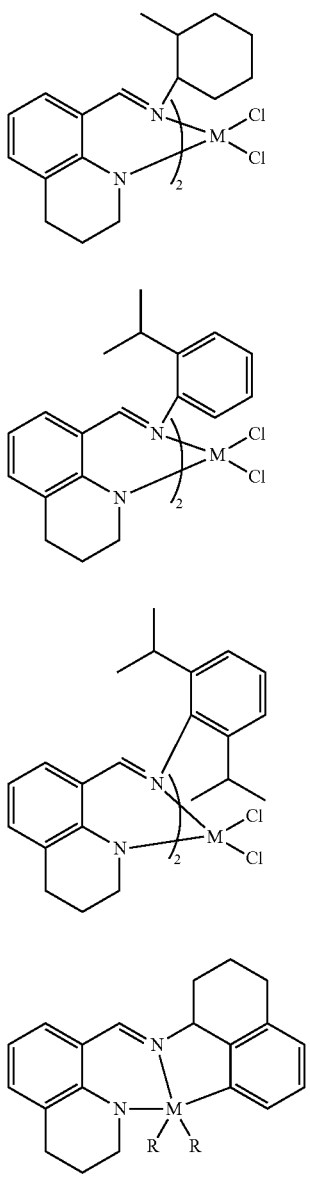

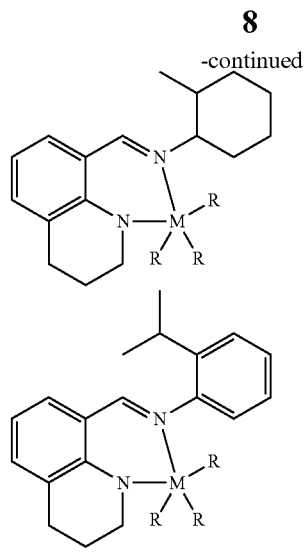

In the above structural formulas, M is a transition metal of Group IV

Rs are the same with or different from each other, and are independently selected from the group consisting of hydrogen, deuterium, a halogen group, a nitrile group, an acetylene group, an amine group, an amide group, an ester group, a ketone group, a C1-C20 alkyl group, a C2-C20 alkenyl group, a C6-C20 aryl group, a C4-C20 heterocyclic group, a C1-C20 alkoxy group, and a C6-C20 aryloxy group, respectively.

As shown in FIG. 4, the catalyst in accordance with the present invention can have a structure wherein the molar ratio between the ligand and the metal is either the same as in the conventional catalyst (i.e., 2:1) or different therefrom (e.g., 1:1). With the structural characteristics as described above, the catalyst of the present invention can have a metal content equal to or higher than that of the conventional catalyst.

A typical production method of the aforementioned metallic compound is the same as set forth hereinafter, but the present invention is not limited thereto.

First, after a certain amount of the ligand represented by Chemical Formula 1 and 1.05 equiv. of a metallic precursor are mixed together, a suitable amount of a toluene solvent is introduced to the resulting mixture at a temperature of −75° C. to −80° C., preferably, at −78° C. and stirred for 6 hours to 2 days while being slowly warmed to room temperature. Then, a desired organometallic compound can be obtained either by eliminating the solvent or as a solution if the amount of the solvent as introduced is known.

A third aspect of the present invention relates to a catalyst composition comprising the foregoing metallic compound, a compound as represented by Chemical Formula 4, and a compound as represented by Chemical Formula 5.

A fourth aspect of the present invention relates to a production method of the catalyst composition, which is characterized in that it comprises the steps of bring the metallic compound into contact with a first cocatalyst represented by Chemical Formula 4 to obtain a mixture; bring the mixture of the metallic compound and the first cocatalyst represented by Chemical Formula 4 into contact with a second cocatalyst represented by Chemical Formula 5.

In the catalyst composition and the production method thereof, the compound as represented by Chemical Formula 4 can be selected from the group consisting of trimethyl aluminum, triethyl aluminum, triisobutyl aluminum, tripropyl aluminum, tributyl aluminum, dimethylchloro aluminum, triisopropyl aluminum, tri-s-butyl aluminum, tricyclopentyl aluminum, tripentyl aluminum, triisopentyl aluminum, trihexyl aluminum, trioctyl aluminum, ethyl dimethyl aluminum, methyl diethyl aluminum, triphenyl aluminum, tri-p-tolyl aluminum, dimethyl aluminum methoxide and dimethyl aluminum ethoxide.

In addition, in the compound represented by Chemical Formula 5, the non-coordinate anion moiety, $[ZA_4]^-$ can be $B[C_6F_5]_4^-$.

Examples of the compound as represented by Chemical Formula 5 include trimethyl ammonium tetrakis(pentafluorophenyl)borate, triethyl ammonium tetrakis(pentafluorophenyl)borate, tripropyl ammonium tetrakis(pentafluorophenyl)borate, tri(n-butyl)ammonium tetrakis (pentafluorophenyl)borate, tri(2-butyl)ammonium tetrakis (pentafluorophenyl)borate, N,N-dimethylanilinium tetrakis (pentafluorophenyl)borate, N,N-dimethylanilinium n-butyltris(pentafluorophenyl)borate, N,N-dimethylanilinium benzyltris(pentafluorophenyl)borate, N,N-dimethylanilinium tetrakis(4-(t-butyldimethylsilyl)-2,3,5,6-tetrafluorophenyl)borate, N,N-dimethylanilinium tetrakis(4-(triisopropylsilyl)-2,3,5,6-tetrafluorophenyl)borate, N,N-dimethylanilinium pentafluorophenoxytris (pentafluorophenyl)borate, N,N-diethylanilinium tetrakis (pentafluorophenyl)borate, N,N-dimethyl-2,4,6-trimethylanilinium tetrakis(pentafluorophenyl)borate, trimethyl ammonium tetrakis(2,3,4,6-tetrafluorophenyl)borate, triethyl ammonium tetrakis(2,3,4,6-tetrafluorophenyl)borate, tripropyl ammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, N,N-dimethyl-2,4,6-trimethylanilinium tetrakis(2,3,4,6-tetrafluorophenyl)borate, decyl dimethyl ammonium tetrakis (pentafluorophenyl)borate, dodecyl dimethyl ammonium tetrakis(pentafluorophenyl)borate, tetradecyl dimethyl ammonium tetrakis(pentafluorophenyl)borate, hexadecyl dimethyl ammonium tetrakis(pentafluorophenyl)borate, octadecyl dimethyl ammonium tetrakis(pentafluorophenyl) borate, eicosyldimethyl ammonium tetrakis(pentafluorophenyl)borate, methyldidecyl ammonium tetrakis(pentafluorophenyl)borate, methyldidodecyl ammonium tetrakis (pentafluorophenyl)borate, methylditetradecyl ammonium tetrakis(pentafluorophenyl)borate, methyldihexadecyl ammonium tetrakis(pentafluorophenyl)borate, methyldioctadecyl ammonium tetrakis(pentafluorophenyl)borate, methyldieicosyl ammonium tetrakis(pentafluorophenyl)borate, tridecyl ammonium tetrakis(pentafluorophenyl)borate, tridodecyl ammonium tetrakis(pentafluorophenyl)borate, tritetradecyl ammonium tetrakis(pentafluorophenyl)borate, trihexadecyl ammonium tetrakis(pentafluorophenyl)borate, trioctadecyl ammonium tetrakis(pentafluorophenyl)borate, trieicosyl ammonium tetrakis(pentafluorophenyl)borate, decyl di(n-butyl) ammonium tetrakis(pentafluorophenyl)borate, dodecyl di(n-butyl) ammonium tetrakis(pentafluorophenyl)borate, octadecyl di(n-butyl) ammonium tetrakis (pentafluorophenyl)borate, N,N-didodecylanilinium tetrakis (pentafluorophenyl)borate, N-methyl-N-dodecylanilinium tetrakis(pentafluorophenyl)borate, methyl di(dodecyl) ammonium tetrakis(pentafluorophenyl)borate, and the like.

For examples of a dialkyl ammonium salt, mentions may be made of di-(i-propyl)ammonium tetrakis(pentafluorophenyl)borate, dicyclohexyl ammonium tetrakis(pentafluorophenyl)borate, and the like.

For examples of a carbonium salt, mentions may be made of tropylium tetrakis(pentafluorophenyl)borate, triphenylmethylium tetrakis(pentafluorophenyl)borate, benzene(diazonium) tetrakis(pentafluorophenyl)borate, and the like.

For examples of particularly preferred cocatalyst, mentions may be made of N,N-dimethylanilinium tetrakis(pentafluorophenyl)borate, tributhyl ammonium tetrakis(pentafluorophenyl)borate, di(octadecyl)methyl ammonium tetrakis(pentafluorophenyl)borate, di(octadecyl)(n-buthyl) ammonium tetrakis(pentafluorophenyl)borate, triphenylmethylium tetrakis(pentafluorophenyl)borate, and tropylium tetrakis(pentafluorophenyl)borate, and the like.

In addition, the ratio between the number of moles of the transition metal in the metallic compound and the number of moles of the compound represented by Chemical Formula 4 is preferably from 1:5 to 1:250. The ratio of the number of moles of the transition metal of the compound represented by Chemical Formula 1 to the Group 13 atom of the compound represented by Chemical Formula 5 is preferably between 1:1 and 1:5. When the ratio between the transition metal compound and aluminum falls in the aforementioned ranges, one can obtain a sufficient effect of the catalyst while avoiding problems that an excess amount of alkyl actually serves as a catalyst poison to cause a side effect and a large amount of aluminum ends up being left behind in the polymer. In addition, when the ratio between the transition metal and the Group 13 atom falls in the aforementioned range, one can prepare a catalyst with a complete activation of the metallic compound at a reasonable cost while avoiding problems that the amount of the second cocatalyst is relatively too small to activate the metallic compound completely, bring about a decrease in the activity of the catalyst composition, as prepared.

Typically, the catalyst composition can be prepared by mixing the components in a proper solvent at a temperature of −100° C. to 300° C., preferably 25° C. to 75° C. For a suitable solvent for the production of the catalyst composition, one can use a hydrocarbon solvent such as pentane, hexane, and heptane; or an aromatic solvent such as benzene and toluene.

The catalyst composition may be separately prepared prior to its use. Otherwise, one can prepare the catalyst composition in the same reaction system for the polymerization by combining the catalyst composition in the presence of the monomers to be polymerized. Preferably, the catalyst is advantageously prepared in a separate step in a suitable solvent prior to being added to a polymerization reactor. If each of the components is added in a different order, one may not obtain the catalyst composition of the present invention. Since the catalyst and the catalyst composition are very sensitive to moisture and oxygen, they should be preferably treated under an inert atmosphere such as nitrogen or argon.

A fifth aspect of the present invention is a process for preparing olefinic polymers, which is characterized in that the catalyst composition is brought into contact with monomers.

The most preferred polymerization process with using the catalyst composition of the present invention is a solution process. Moreover, such composition can be adopted in a slurry or gaseous process when being used together with an inorganic carrier such as silica.

The catalyst composition of the present invention can be injected after being dissolved or diluted in a solvent suitable for an olefin polymerization process including an aliphatic hydrocarbon solvent such as pentane, hexane, heptane, nonane, decane, and their isomers, an aromatic hydrocarbon solvent such as toluene and benzene, a chlorinated hydrocarbon solvent such as dichloromethane and chlorobenzene, and the like. It is preferable that the solvent be used after being treated with a small amount of an alkyl aluminum so as to eliminate a small amount of water or air, which may act as a catalyst poison.

Suitable solvents for the polymerization are an inert liquid. For examples of the inert liquid, mentions may be made of hydrocarbons such as isobutane, butane, pentane, hexane, heptane, octane and a mixture thereof; and aromatic compounds such as benzene and toluene. In addition, liquid olefins capable of acting as a monomer or comonomer such as ethylene, propylene, butadiene, cyclopentene, 1-hexene, 3-methyl-1-pentene, 1,4-hexadiene, 1-octene, 1-decene, styrene, and ethylidene norbornene may be included. In addition, a mixture of the foregoing compounds may be included.

For examples of monomers that can be polymerized by using the catalyst composition, mentions may be made of at least one selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-itocene, α-olefins, cyclic olefins, diene olefins and triene olefins.

Specific examples of the monomers include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbornadiene, ethylidene norbornene, phenyl norbornene, vinyl norbornene, dicyclopentadiene, 1,4-butadiene, 1,5-pentadiene, 1,6-hexadiene, styrene, α-methyl styrene, divinyl benzene, and 3-chloromethyl styrene. It is also possible to copolymerize a mixture of at least two of the foregoing monomers.

Most of the polymerization reaction may occur by using such monomers at a temperature of 0° C. to 200° C., preferably 25° C. to 160° C., under a pressure of atmospheric pressure to 1000 psi, preferably 15 psi to 700 psi. The amount of the catalyst used is preferably $10^{-12}$ to $10^{-1}$ mole, more preferably, $10^{-9}$ to $10^{-5}$ mole, per one mole of the monomer.

In particular, the activating composition of the present invention makes it possible for ethylene and sterically-hindered monomers such as 1-octene to be co-polymerized even at a high reaction temperature of at least 90° C. Therefore, in addition to its high molecular weight, the resulting copolymer has a significantly broadened molecular weight distribution in comparison with the polymers prepared by using the conventional metallocene catalyst, and thus one can prepare a product with an enhanced processability. Moreover, one can control the molecular weight and the molecular weight distribution by changing the catalyst.

More specifically, monomers that constitute the copolymer is preferably at least one selected from the group consisting of ethylene and propylene, 1-butene, 1-hexene, and 4-methyl-1-pentene, 1-octene, styrene, and ethylidene norbornene.

MODE FOR PRACTICING THE INVENTION

Hereinafter, preferred examples will be set forth for better understanding of the present invention. The following examples are merely illustrative of the present invention, and the scope of the present invention should not be construed to be defined thereby.

EXAMPLE

The term "overnight" denotes a period of about 12 to 16 hours, and "room temperature" refers to a temperature of 20° C. to 25° C. All processes for synthesis of metal complex and experimentations were conducted under a dry nitrogen atmosphere by using a dry box technique or glassware in which a dry state was maintained. In any case, HPLC grade solvents were used, which had been dried prior to use.

Example 1

Preparation of (E)-N-((1,2,3,4-tetrahydroquinolin-8-yl)methylene)-2-methylcyclohexanamine 1.06 g of tetrahydroquinolino aldehyde was dissolved in 17 ml of methanol and then 1.3 ml of cyclohexyl amine was slowly added thereto. After the mixture was stirred at room temperature overnight, the solvent was eliminated under a reduced pressure and the resulting product was dissolved again in hexane to provide a thick solution, which was then kept in a freezer. In this solution, two types of stereomeric products were mixed at a ratio of 1.5:1. After the solution was left alone for about two days, a white crystalline solid product was found to be formed. The same procedures were repeated with the remaining mother liquor and all of the solid products thus obtained were collected and washed with cold methanol and hexane, and then dried to provide a pure stereomeric product. (Yield: 50%)

1H NMR (500 MHz, d-toluene): 0.83 (d, J=7 Hz, 3H, CH3), 0.95-1.01 (m, 1H, CH), 1.20-1.29 (m, 2H, CH2), 1.52-1.71 (m, 8H, CH2), 2.09-2.10 (m, d-tol), 2.38-2.43 (m, 1H, CH), 2.51-2.53 (m, 2H, CH2), 3.12-3.13 (m, 2H, CH2), 6.55 (t, J=7.5 Hz, 1H, phenyl), 6.83 (d, J=7.5 Hz, 1H, phenyl), 6.97-7.01 (m, 1H, phenyl, d-tol), 7.10 (s, d-tol), 8.16 (s, 1H, CH), 9.27 (b, 1H, NH).

Example 2

Preparation of 1,2,3,4-tetrahydro-N-((1,2,3,4-tetrahydroquinolin-8-yl)methylene)-naphthalen-1-amine 0.57 g of tetrahydroquinolino aldehyde was dissolved in 10 ml of methanol and then 0.51 ml of 1,2,3,4-tetrahydro naphthyl amine was slowly added thereto. The resulting mixture was stirred at room temperature overnight before some precipitates were slowly formed. Then, the resulting mixture was filtered while being washed with methanol to provide ivory solids as a clean product (0.72 g). (Yield: 70%)

1H NMR (500 MHz, d-toluene): 1.44-1.48 (m, 2H, CH2), 1.64-1.69 (m, 1H, CH2), 1.83-1.85 (m, 1H, CH2), 1.86-1.96 (m, 2H, CH2), 2.46-2.49 (m, 2H, CH2), 2.60-2.64 (m, 1H, CH2), 2.65-2.69 (m, 1H, CH2), 2.87-2.89 (m, 1H, CH2), 2.92-2.97 (m, 1H, CH2), 4.11-4.13 (m, 1H, CH), 6.56 (t, J=7.5 Hz, 1H, phenyl), 6.83 (d, J=7.5 Hz, 1H, phenyl), 6.96-7.10 (m, 5H, phenyl), 8.27 (s, 1H, CH), 9.20 (b, 1H, NH).

Example 3

Preparation of 1,2,3,4-tetrahydro-N-((2-methylindolin-7-yl)methylene)-naphthalen-1-amine 1.68 g of 2-methylindolino aldehyde was dissolved in 35 ml of methanol and then 1.58 ml of 1,2,3,4-tetrahydro naphthyl amine was slowly added thereto. The mixture was stirred at room temperature overnight before some precipitates were slowly formed, and then was filtered while being washed with methanol to provide ivory solids as a clean product (2.3 g). (Yield: 75%) This compound was a mixture of two stereoisomers at a ratio of 1:0.6.

1H NMR (500 MHz, d-toluene): 0.81 & 0.88 (d, J=6 Hz, 3H, CH3), 1.65-1.72 (m, 1H, CH2), 1.82-1.86 & 1.87-1.98 (m, 3H, CH2), 2.26-2.31 (m, 1H, CH2), 2.60-2.83 (m, 3H, CH2), 3.59-3.62 & 3.68-3.72 (m, 1H, CH), 4.16-4.19 (m, 1H, CH), 6.60-6.64 (m, 1H, phenyl), 6.89-7.14 (m, 6H, phenyl), 7.14 & 7.19 (b, 1H, NH), 8.21 (s, 1H, CH).

Example 4

Preparation of Zirconium Catalyst I

In a Glove box, 145 mg of the ligand obtained from Example 2 and 231 mg of benzyl zirconium were measured and put into a Schlenk flask. Thereafter, the Schlenk flask was taken out and cooled to −78° C., and at that temperature, 12 ml of toluene was slowly added thereto. The resulting mixture was gradually warmed to room temperature while being stirred for 6 hours to obtain a dark orange toluene solution as a product solution. Then, the solvent was eliminated from the solution, and thereby the pure product was obtained. For a large scale synthesis, it would be convenient that a calculated amount of toluene is injected thereto without elimination of the solvent such that the product is obtained and used in the form of a toluene solution.

1H NMR (500 MHz, d-toluene): 1.09-1.13 (m, 1H, CH3), 1.50-1.61 (m, 1H, CH2), 1.65-1.75 (m, 4H, CH2), 2.31 (d, J=10.5 Hz, 1H, CH2Ph), 2.49-2.61 (m, 6H, CH2 and CH2Ph), 2.67 (d, J=10.5 Hz, 1H, CH2Ph), 3.18-3.24 (m, 1H, CH2), 3.56-3.62 (m, 1H, CH2), 4.30-4.34 (m, 1H, CH), 6.55-7.23 (m, 15H, phenyl), 7.97 (s, 1H, imide CH), 8.13 (d, J=7 Hz, 1H, phenyl).

Example 5

Preparation of Zirconium Catalyst II

In a Glove box, 90 mg of the ligand obtained from Example 1 and 169 mg of benzyl zirconium were measured and put into a Schlenk flask. Thereafter, the Schlenk flask was taken out and cooled to −78° C., and at that temperature, 10 ml of toluene was slowly added thereto. The resulting mixture was then gradually warmed to room temperature while being stirred for 2 days to obtain a dark orange toluene solution as a product solution. Only a sticky solution could be obtained even when the solvent was completely eliminated. Accordingly, in light of possible difficulties in handling, it would be advantageous to obtain the product as a solution.

1H NMR (500 MHz, d-toluene): 0.41 (d, J=7 Hz, 3H, CH3), 0.83-1.03 (m, 4H, CH2), 1.18-1.31 (m, 2H, CH2), 1.40-1.62 (m, 5H, CH2), 1.83-1.88 (m, 1H, CH), 2.05-2.12 (m, d-tol, CH2), 2.47-2.55 (m, 8H, CH2), 3.21-3.25 (m, 1H, CH), 3.38-3.41 (m, 1H, CH), 3.79-3.83 (m, 1H, CH), 6.58 (t, J=7.5 Hz, 1H, phenyl), 6.82-7.12 (m, phenyl, d-tol), 8.07 (s, 1H, CH).

Example 6

High Pressure Ethylene Polymerization

To a 2 L autoclave reactor was added 0.1 L of hexane as a solvent, and then the reactor was pre-heated to 100° C. A 25 mL catalyst storage tank was filled with 5.0 mmol of a catalyst compound treated with 125 mmol of triisobutyl aluminum compound and 25 mmol of cocatalyst of trityl tetrakis(pentafluorophenyl)borate one by one. At this time, ethylene was put into the catalyst tank until its pressure reached 30 bar and Catalyst I was injected into the reactor by using a high pressure argon and a polymerization reaction was conducted for 10 minutes. Then, the remaining ethylene gas was get out, and an excess amount of ethanol was added to the polymer solution thus obtained to induce a precipitation. The resulting polymer was washed with ethanol and acetone two to three times, respectively, and dried in a vacuum oven at 80° C. for at least 12 hours. The weight as measured for the polymer and the characterization results thereof were set forth in Table 1.

Example 7

High Pressure Ethylene Polymerization

Except that the polymerization temperature was set to be 120° C., the experimentation was conducted under the same condition as in Example 4.

Example 8

High Pressure Copolymerization of Ethylene and 1-Octene

To a 2 L autoclave reactor were added 0.1 L of hexane as a solvent and 144 ml of a 1-octene solution (0.8M) diluted/prepared with hexane, and then the reactor was pre-heated to 100° C. A 25 mL catalyst storage tank was filled with 5.0 mmol of a titanium compound treated with 125 mmol of triisobutyl aluminum compound and 25 mmol of cocatalyst of trityl tetrakis(pentafluorophenyl)borate one by one. At this time, ethylene was put into the catalyst tank until its pressure reached 30 bar and the catalyst was injected into the reactor by using a high pressure argon and a copolymerization reaction was conducted for 10 minutes. Then, the remaining ethylene gas was get out and an excess amount of ethanol was added to the polymer solution thus obtained to induce a precipitation. The resulting polymer was washed with ethanol and acetone two to three times, respectively, and dried in a vacuum oven at 80° C. for at least 12 hours. The weight as measured for the polymer and the characterization results thereof were set forth in Table 1.

Example 9

High Pressure Ethylene Polymerization

Except that Catalyst II was used, the experimentation was conducted under the same condition as in Example 6.

Example 10

Copolymerization of Ethylene and 1-Octene

Except that the polymerization temperature was set to be 120° C. and Catalyst II was used, the experimentation was conducted under the same condition as in Example 8.

Example 11

Copolymerization of Ethylene and 1-Octene

Except that the polymerization temperature was set to be 100° C. and Catalyst II was used, the experimentation was conducted under the same condition as in Example 8.

Comparative Example 1

Copolymerization of Ethylene and 1-Octene

Except that a zirconium catalyst from Dow Co. Ltd. was used, the experimentation was conducted under the same condition as in Example 8.

Experimental Examples

For the polymers as prepared in the examples and the comparative examples, evaluation was made according to the following methods and the results were set forth in Table 1. In Table 1, the results of the ethylene polymerization and the copolymerization of ethylene and 1-octene were shown.

1. Molecular Weight Distribution (Polydispersity Index: PDI)

A number average molecular weight (Mn) and a weight average molecular weight (Mw) were measured by using Gel Permeation Chromatography (GPC) and then the polydispersity index was calculated by dividing the weight average molecular weight (Mw) by the number average molecular weight (Mn).

2. Melting Temperature (Tm)

The polymer was heated to a temperature of 200° C. and the temperature was maintained for 5 minutes. Then, the polymer cooled to 30° C. and was heated again. The melting temperature was determined as the top of the DSC curve (Differential Scanning Calorimeter manufactured by TA Co.). In this regard, the heating and cooling rates were 10° C./min, respectively. The melting temperature was determined by using the results measured in the second heating cycle.

TABLE 1

| item | Activity (Kg/mmol-cat hr) | Mw | PDI | melting temp. (° C.) |
|---|---|---|---|---|
| Example 6 | 26.2 | 450,873 | 4.32 | 137 |
| Example 7 | 13.6 | 391,728 | 13.8 | 132 |
| Example 8 | 77.6 | 318,991 | 3.76 | 126 |
| Example 9 | 40.3 | 136,480 | 2.30 | 138 |
| Example 10 | 39.0 | 138,547 | 2.24 | 128 |
| Example 11 | 75.1 | 101,609 | 2.71 | 125 |
| Comp. Example 1 (Dow Zirconium catalyst) | 12.6 | 87,460 | 2.8 | 133 |

With reference to Table 1, the ethylene polymers prepared from Examples 6 to 8 have the production amount equal to or higher than the ethylene polymers prepared from Comparative Example 1. In addition, they have a broad molecular weight distribution and their weight average molecular weight was much higher than that of Comparative Example 1. By contrast, the ethylene polymers and the ethylene/1-octene copolymers prepared from Examples 9 to 11 were found to have a narrowed molecular weight distribution and their molecular weight was found to decrease to some extent, as well. In particular, in the case of the ethylene/1-octene copolymers prepared in Example 8 and Example 11, their activities were 7 times higher than that of Comparative Example 1, and their melting temperatures were slightly decreased, and it was also found that the weight average molecular weight and the polydispersity index could be controlled by the types of the catalyst.

What is claimed is:

1. A compound as represented by Chemical Formula 1:

[Chemical Formula 1]

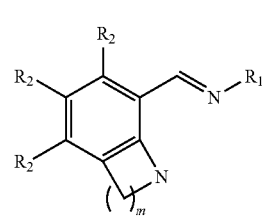

in Chemical Formula 1, m is an integer of 1 to 7;

$R_1$ is a C4-C10 cycloalkyl group substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group and a C4-C20 heterocyclic group; a C2-C9 heterocyclic group with a heteroatom of O, N or S, substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group; a C6-C10 aryl group substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group; or a C5-C10 heteroaryl group with a heteroatom of O, N or S, substituted with at least one group selected from the group consisting of hydrogen, deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group, wherein when the $R_1$ is substituted with at least two groups, the groups that are adjacent to each other can form an aliphatic or aromatic condensed ring;

$R_2$s are the same with or different from each other, and are independently selected from the group consisting of hydrogen, deuterium, a halogen group, a nitrile group, an acetylene group, an amine group, an amide group, an ester group, a ketone group, a C1-C20 alkyl group, a C2-C20 alkenyl group, a C6-C20 aryl group, a C4-C20 heterocyclic group, a C1-C20 alkoxy group, and a C6-C20 aryloxy group, respectively, and at least two of the $R_2$ can be linked to each other to form an aliphatic or aromatic ring.

2. The compound according to claim 1, wherein the compound is represented by Chemical Formula 2 or Chemical Formula 3:

[Chemical Formula 2]

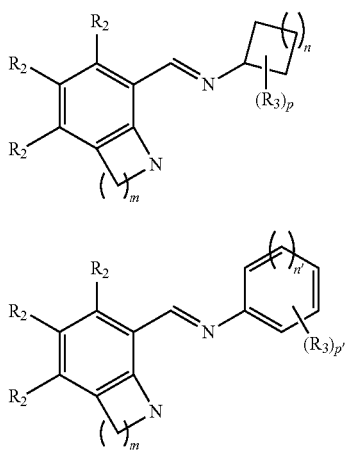

[Chemical Formula 3]

In Chemical Formula 2 or Chemical Formula 3, m and R$_2$ are the same as defined in Chemical Formula 1, n is an integer of 1 to 7, n' is an integer of 1 to 5, p is an integer of 0 to 2+n, p' is an integer of 0 to 5+n', and R$_3$s are the same with or different from each other, and are independently selected from the group consisting of deuterium, a halogen group, a nitrile group, an acetylene group, an amine group, an amide group, an ester group, a ketone group, a C1-C20 alkyl group, a C6-C20 cycloalkyl group, a C2-C20 alkenyl group, a C6-C20 aryl group, a silyl group, a C7-C20 alkylaryl group, a C7-C20 arylalkyl group, and a C4-C20 heterocyclic group, and at least two of the R3s can be linked to each other to form an aliphatic or aromatic condensed ring.

3. The compound according to claim 2, wherein m is 2 or 3.

4. The compound according to claim 2, wherein n is 2 or 3.

5. The compound according to claim 2, wherein n' is an integer of 1 to 3.

6. The compound according to claim 2, wherein R$_3$ is a C1-C20 alkyl group, a C6-C20 cycloalkyl group, a C2-C20 alkenyl group, or a C6-C20 aryl group and at least two of the R$_3$s can be linked to each other to form an aliphatic or aromatic condensed ring.

7. The compound according to claim 1, wherein the compound is represented by one of the following structural formulas:

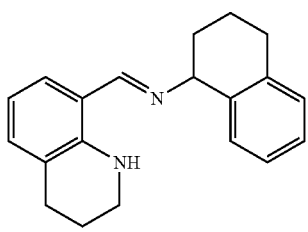

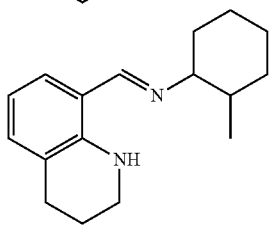

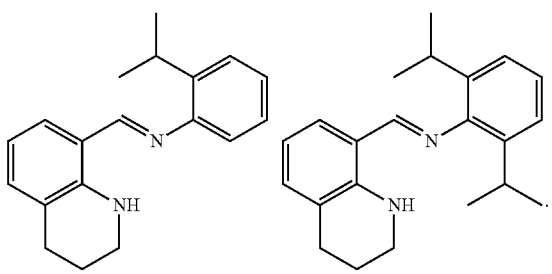

8. A metallic compound coordinated by a transition metal of Group IV, which comprises a compound in accordance with claim 1 as a ligand.

9. The metallic compound according to claim 8, wherein the transition metal is selected from the group consisting of Ti, Zr, and Hf.

10. The metallic compound according to claim 8, wherein the metallic compound is represented by any one of the following structural formulas:

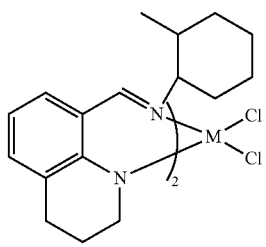

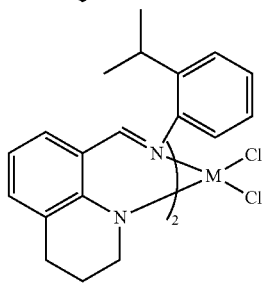

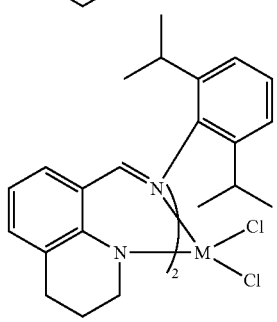

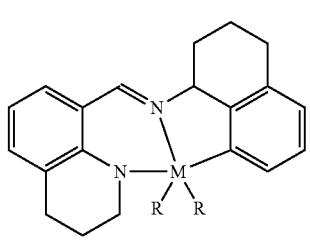

-continued

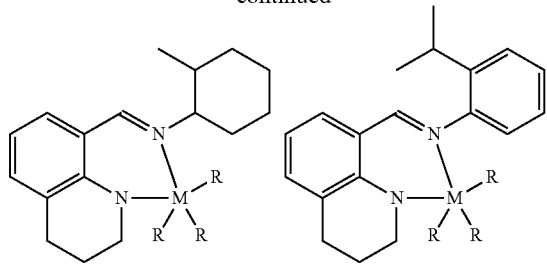

in the above formulas, M is a transition metal of Group IV, and Rs are the same with or different from each other, and are independently selected from the group consisting of hydrogen, deuterium, a halogen group, a nitrile group, an acetylene group, an amine group, an amide group, an ester group, a ketone group, a C1-C20 alkyl group, a C2-C20 alkenyl group, a C6-C20 aryl group, a C4-C20 heterocyclic group, a C1-C20 alkoxy group, and a C6-C20 aryloxy group, respectively.

11. A catalyst composition comprising a metallic compound of claim 8, a compound represented by Chemical Formula 4, and a compound represented by Chemical Formula 5:

$Al(R_3)_3$ [Chemical Formula 4]

in the above formula, $R_3$s are independently a halogen radical or a C1-C20 hydrocarbyl radical unsubstituted or substituted with a halogen, respectively;

$[L-H]^+[ZA_4]^-$ or $[L]^+[ZA_4]^-$ [Chemical Formula 5]

in the above formulas, L is a neutral or cationic Lewis base; and H is a hydrogen atom; Z is an element of Group 13; and As are independently a C6-C20 aryl or an alkyl radical substituted with a halogen, a C1-C20 hydrocarbyl, an alkoxy, or a phenoxy radical for at least one hydrogen atom therein.

12. The catalyst composition according to claim 11, wherein the compound represented by Chemical Formula 4 is selected from the group consisting of trimethyl aluminum, triethyl aluminum, triisobutyl aluminum, tripropyl aluminum, tributyl aluminum, dimethyl chloro aluminum, triisopropyl aluminum, tri-s-butyl aluminum, tricyclopentyl aluminum, tripentyl aluminum, triisopentyl aluminum, trihexyl aluminum, trioctyl aluminum, ethyl dimethyl aluminum, methyl diethyl aluminum, triphenyl aluminum, tri-p-tolyl aluminum, dimethyl aluminum methoxide, and dimethyl aluminum ethoxide.

13. The catalyst composition according to claim 11, wherein a non-coordinating anion of the compound represented by Chemical Formula 5, $[ZA_4]^-$ is $B[C_6F_5]_4^-$.

14. A method of producing a catalyst composition, which comprises the steps of bringing a metallic compound of claim 8 into contact with a first cocatalyst represented by Chemical Formula 4 to make a mixture; and bringing the mixture of the metallic compound and the first cocatalyst into contact with a second cocatalyst represented by Chemical Formula 5:

$Al(R_3)_3$ [Chemical Formula 4]

in the above formula, $R_3$s are independently a halogen radical, mehtoxy radical, ethoxy radical, or a C1-C20 hydrocarbyl radical unsubstituted or substituted with a halogen, respectively;

$[L-H]^+[ZA_4]^-$ or $[L]^+[ZA_4]^-$ [Chemical Formula 5]

in the above formula, L is a neutral or cationic Lewis base; and H is a hydrogen atom; Z is an element of Group 13; and As are independently a C6-C20 aryl or an alkyl radical substituted with a halogen, a C1-C20 hydrocarbyl, an alkoxy, or a phenoxy radical for at least one hydrogen atom therein.

15. The method of producing a catalyst composition according to claim 14, wherein the mole ratio of the transition metal in the metallic compound to the compound represented by Chemical Formula 4 is from 1:5 to 1:250, and the mole ratio of the transition metal of the compound represented by Chemical Formula 1 to the Group 13 atom of the compound represented by Chemical Formula 5 is between 1:1 and 1:5.

16. The method of producing a catalyst composition according to claim 14, wherein the compound represented by Chemical Formula 4 is selected from the group consisting of trimethyl aluminum, triethyl aluminum, triisobutyl aluminum, tripropyl aluminum, tributyl aluminum, dimethyl chloro aluminum, triisopropyl aluminum, tri-s-butyl aluminum, tricyclopentyl aluminum, tripentyl aluminum, triisopentyl aluminum, trihexyl aluminum, trioctyl aluminum, ethyl dimethyl aluminum, methyl diethyl aluminum, triphenyl aluminum, tri-p-tolyl aluminum, dimethyl aluminum methoxide, and dimethyl aluminum ethoxide.

17. The method of producing a catalyst composition according to claim 14, wherein a non-coordinating anion of the compound represented by Chemical Formula 5, $[ZA_4]^-$ is $B[C_6F_5]_4^-$.

18. A process for preparing olefin polymers, which is characterized in that a catalyst composition of claim 11 bringing into contact with a monomer.

19. The process for preparing olefin polymers according to claim 18, wherein the monomer is at least one olefin selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, and 1-hexadecene, α-olefins, cyclic olefins, diene olefins, and triene olefins.

* * * * *